United States Patent
Zimmer et al.

(10) Patent No.: US 7,109,214 B2
(45) Date of Patent: Sep. 19, 2006

(54) SUBSTITUTED CYCLOPENTENE COMPOUNDS

(75) Inventors: Oswald Zimmer, Würselen (DE); Michael Haurand, Aachen (DE); Klaus Schiene, Düsseldorf (DE); Clemens Gillen, Aachen (DE); Johannes Schneider, Stolberg (DE); Gregor Bahrenberg, Aachen (DE)

(73) Assignee: Grunenthal GmbH, Aachen (DE)

( * ) Notice: Subject to any disclaimer, the term of this patent is extended or adjusted under 35 U.S.C. 154(b) by 0 days.

(21) Appl. No.: 10/993,545

(22) Filed: Nov. 19, 2004

(65) Prior Publication Data

US 2005/0272955 A1 Dec. 8, 2005

(30) Foreign Application Priority Data

Jun. 9, 2004 (DE) ...................... 10 2004 027 912

(51) Int. Cl.
*A01N 43/40* (2006.01)

(52) U.S. Cl. ...................... 514/315; 514/317; 514/319; 514/520; 514/521; 549/474; 546/251; 544/183; 544/239; 548/243; 558/409

(58) Field of Classification Search ................ 514/315, 514/317, 319, 520, 521; 558/409; 549/474; 546/251; 544/183, 239; 548/243; 564/396, 564/397, 398
See application file for complete search history.

(56) References Cited

U.S. PATENT DOCUMENTS

| | | | | |
|---|---|---|---|---|
| 5,698,584 | A | 12/1997 | Black et al. | 514/462 |
| 5,700,816 | A | 12/1997 | Isakson et al. | 514/326 |
| 6,057,319 | A * | 5/2000 | Black et al. | 514/242 |
| 6,222,048 | B1 * | 4/2001 | Black et al. | 549/60 |

FOREIGN PATENT DOCUMENTS

| WO | WO 95/18799 | 7/1995 |
|---|---|---|
| WO | WO 97/28121 | 8/1997 |
| WO | WO 98/56779 | 12/1998 |
| WO | WO 01/56382 A1 | 8/2001 |
| WO | WO 2004/002420 A2 | 1/2004 |

OTHER PUBLICATIONS

"Efficient Syntheses of 2-(3',5'-Difluorophenyl)-3-(4'-methylsulfonylphenyl)-cyclopent-2-enome, a Potent COX-2 Inhibitor", Dalian Zhao, et al., Tetrahedron 55 (1999) 6001-6018.
"Weighing and Measuring", Metrology and Calculation, pp. 76-91.
"A Potent and Selective Cgrp$_2$ Agonist, [Cys(Et)$_{2,7}$]Hcgpr$\alpha$: Comparison In Prototypical Cgrp$_2$ In Vitro Bioassays[1]" Yvan Dumont, et al., Can. J. Physiol. Pharmacol. 75: 671-676 (1997).
"Efficient Synthesis of 2-(3',5'-Difluorophenyl)-3-(4'-Methylsulfonylphenyl)-Cyclopent-2-Enone, A Potent Cox-2 Inhibitor", Dalian Zhao, et al., Tetrahedron 55 (1999) 6001-6018.
"2,3-Diarylcyclopentenones as Orally Active, Highly Selective Cyclooxygenase-2 Inhibitors", W. Cameron Black, et al., J. Med. Chem. 1999, 42, 1274-1281.
"A Novel High Throughput Chemiluminescent Assay for the Measurement of Cellular Cyclic Adenosine Monophosphate Levels", Anthony C. Chiulli, et al., Journal of Biomolecular Screening, vol. 5, No. 4, 2000., 239-247.
"Organikum", Heinz G. O. Becker, et al., ISBN 3-335-00343-8, 1993, 422-424.
"Calcitonin gene-related peptide (CGRP) receptors are linked to cyclic adenosine monophosphate production in SK-N-MC human neuroblastoma cells", F. Van Valem, et al., Neuroscience Letters, 199 (1990) 195-198.

* cited by examiner

Primary Examiner—Johann Richter
Assistant Examiner—Chukwuma Nwaonicha
(74) Attorney, Agent, or Firm—Perman & Green, LLP.

(57) ABSTRACT

The present invention relates to substituted cyclopentene compounds of the general formula I, to a process for the production thereof, to pharmaceutical preparations containing these compounds and to the use thereof for the production of pharmaceutical preparations.

51 Claims, No Drawings

SUBSTITUTED CYCLOPENTENE COMPOUNDS

CROSS-REFERENCE TO RELATED APPLICATIONS

This applications claims priority from German Patent Application No. 10 2004 027 912.8 filed Jun. 6, 2004.

BACKGROUND OF THE INVENTION

1. Field of the Invention

The present invention relates to substituted cyclopentene compounds of the general formula I, to a process for the production thereof, to pharmaceutical preparations containing these compounds and to the use thereof for the production of pharmaceutical preparations.

2. Brief Description of Related Developments

The neuropeptide α-CGRP (α-calcitonin gene-related peptide) consisting of 37 amino acids arises by alternative splicing of the calcitonin gene. Another CGRP, β-CGRP, is furthermore known, which exhibits elevated sequence analogy with α-CGRP, but is transcribed from another gene.

These neuropeptides are stored in or released from the nerve ends of the central and peripheral nervous system and exert their physiological action by binding to specific G-protein-coupled receptors known as CGRP receptors. These CGRP receptors, various subtypes of which such as CGRP1 and CGRP2 are known, are located on the surface of cells of various tissues, such as for example muscle cells, glandular cells, epithelial cells or neuronal cells.

Given the widespread distribution of CGRP receptors in tissues of various specialisations, the CGRP peptide receptor system is of central significance in numerous physiological and pathophysiological processes, such as for example processes of the cardiovascular system, of the central and/or peripheral nervous system, of the respiratory system or of the endocrine system. For example, patients with acute migraine and those with cluster headaches have a plasma concentration of the neuropeptide CGRP which is higher than that of a healthy comparison group.

The regulation of CGRP receptors, in particular the inhibition of CGRP receptors with the assistance of a receptor-specific antagonist, accordingly opens up a new approach for the successful treatment of disorders and diseases associated with the CGRP ligand-receptor system.

The object of the present invention was accordingly to provide novel compounds which are in particular suitable as pharmaceutical active ingredients in pharmaceutical preparations. These compounds should preferably be suitable for regulating the CGRP receptor, in particular as an antagonist for the inhibition of CGRP receptors. These compounds should likewise preferably be suitable for the treatment and/or prevention of disorders and/or diseases, which are at least partially mediated by the CGRP receptor, preferably by the CGRP-1 receptor, for the prevention and/or treatment of pain, preferably of acute pain, chronic pain, chronic inflammatory pain and/or visceral pain, cluster headaches, neurovascular disorders, migraine, preferably of migraine with aura, migraine without aura, common migraine, classic migraine or complicated migraine, inflammation, preferably pulmonary inflammation, asthma, arthritis, hypertonia, hypotonia, tachycardia, non-insulin-dependent diabetes mellitus, cardiovascular diseases, skin conditions and/or skin damage, preferably skin damage caused by heat and/or radiation, particularly preferably skin damage caused by sunburn, allergic rhinitis, diseases which accompany overshooting vascular dilation, preferably shock or sepsis, menopausal hot flushes or opioid tolerance, preferably morphine tolerance.

It has surprisingly now been found that the substituted cyclopentene compounds according to the invention of the general formula I below exhibit an elevated affinity for the CGRP receptor and are suitable as antagonists, in particular for the inhibition of the CGRP receptor, preferably of the CGRP1 receptor.

SUMMARY OF THE INVENTION

The present invention accordingly provides substituted cyclopentene compounds of the general formula I

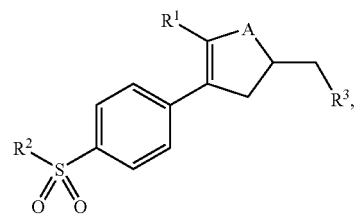

in which
$R^1$ denotes an optionally at least mono-substituted phenyl residue, which may be condensed (fused) with an optionally at least mono-substituted, saturated, unsaturated or aromatic monocyclic ring system optionally comprising at least one heteroatom as a ring member,
$R^2$ denotes a linear or branched alkyl residue or an —NH$_2$ group,
$R^3$ denotes an —NR$^4$R$^5$ group or an —NR$^6$R$^7$ group,
$R^4$ and $R^5$, identical or different, in each case denote hydrogen or a linear or branched alkyl residue, with the proviso that the two residues $R^4$ and $R^5$ do not simultaneously mean hydrogen,
$R^6$ and $R^7$, together with the nitrogen atom bridging them as a ring member, form a saturated, optionally at least mono-substituted, heterocyclic residue optionally comprising at least one further heteroatom as a ring member,
A denotes a C(=O) group or a C(H)(R$^8$) group,
$R^8$ denotes an OH group or an —O—(C=O)—R$^9$ group,
$R^9$ denotes a linear or branched alkyl residue,
in each case optionally in the form of the pure stereoisomers thereof, in particular enantiomers or diastereomers, the racemates thereof or in the form of mixtures of the stereoisomers, in particular of the enantiomers and/or diastereomers, in any desired mixing ratio, or in each case in the form of corresponding salts or in each case in the form of corresponding solvates.

For the purposes of the present invention, a monocyclic ring system is taken to mean monocyclic hydrocarbon residues, which may be saturated, unsaturated or aromatic. The monocyclic ring system may optionally also comprise one or more heteroatoms as ring members, wherein the heteroatoms may be identical or different and in each case are preferably selected from the group consisting of oxygen, nitrogen and sulfur. The monocyclic ring system preferably comprises 5 or 6 ring members.

If $R^1$ denotes an at least mono-substituted phenyl residue and/or comprises an at least mono-substituted, saturated, unsaturated or aromatic monocyclic ring system optionally comprising at least one heteroatom as a ring member, the respective substituents may, in each case mutually independently, preferably be selected from the group consisting of halogen, OH, $CF_3$, $CF_2H$, $CFH_2$, a linear or branched $C_{1-4}$ alkyl residue, —$SO_2R^A$, in which $R^A$ denotes an $NH_2$ group or a linear or branched $C_{1-4}$ alkyl residue, and $OR^B$, in which $R^B$ denotes a linear or branched $C_{1-4}$ alkyl residue, particularly preferably from the group consisting of F, Cl, Br, methyl, ethyl, n-propyl, iso-propyl, n-butyl, sec-butyl, tert-butyl, OH, $CF_3$, $OCH_3$, $OCH_2CH_3$, $SO_2NH_2$ and $SO_2CH_3$, very particularly preferably from the group consisting of F, Cl, methyl, ethyl, iso-propyl, tert-butyl, OH, $CF_3$, $OCH_3$, $OCH_2CH_3$, and $SO_2CH_3$.

If residues $R^6$ and $R^7$, together with the nitrogen atom bridging them as a ring member, form a saturated, at least mono-substituted, heterocyclic residue optionally comprising at least one further heteroatom as a ring member, the respective substituents may, in each case mutually independently, preferably be selected from the group consisting of halogen, OH, $CF_3$, $CF_2H$, $CFH_2$, a linear or branched $C_{1-4}$ alkyl residue, —$SO_2R^A$, in which $R^A$ denotes an $NH_2$ group or a linear or branched $C_{1-4}$ alkyl residue, and $OR^B$, in which $R^B$ denotes a linear or branched $C_{1-4}$ alkyl residue, particularly preferably from the group consisting of F, Cl, Br, methyl, ethyl, n-propyl, iso-propyl, n-butyl, sec-butyl, tert-butyl, OH, $CF_3$, $OCH_3$, $OCH_2CH_3$, $SO_2NH_2$ and $SO_2CH_3$, very particularly preferably from the group consisting of F, Cl, methyl, ethyl, iso-propyl, tert-butyl, OH, $CF_3$, $OCH_3$, $OCH_2CH_3$, and $SO_2CH_3$. If the heterocyclic residue comprises one or more further heteroatoms, these may preferably be selected from the group consisting of oxygen, nitrogen and sulfur. Oxygen and/or nitrogen may particularly preferably be present as further heteroatoms.

Preferred substituted cyclopentene compounds of the general formula I are those in which $R^1$ denotes an optionally at least mono-substituted phenyl residue, which may be condensed with an optionally at least mono-substituted, saturated, unsaturated or aromatic 5-or 6-membered monocyclic ring system optionally comprising at least one heteroatom as a ring member, preferably denotes an optionally at least mono-substituted phenyl, naphthyl or benzo-[1,3]-dioxole residue, and in each case the remaining residues $R^2$–$R^9$ and A have the above-stated meaning, optionally in each case in the form of the pure stereoisomers thereof, in particular enantiomers or diastereomers, the racemates thereof or in the form of mixtures of the stereoisomers, in particular the enantiomers and/or diastereomers, in any desired mixing ratio, or in each case in the form of corresponding salts or in each case in the form of corresponding solvates.

Further preferred substituted cyclopentene compounds of the general formula I are those in which $R^2$ denotes a linear or branched $C_{1-6}$ alkyl residue or an —$NH_2$ group, preferably a linear or branched $C_{1-4}$ alkyl residue or an $NH_2$ group, particularly preferably for a methyl residue, an ethyl residue or an $NH_2$ group, very particularly preferably a methyl residue, and in each case the remaining residues $R^1$, $R^3$–$R^9$ and A have the above-stated meaning, optionally in each case in the form of the pure stereoisomers thereof, in particular enantiomers or diastereomers, the racemates thereof or in the form of mixtures of the stereoisomers, in particular the enantiomers and/or diastereomers, in any desired mixing ratio, or in each case in the form of corresponding salts or in each case in the form of corresponding solvates.

Other preferred substituted cyclopentene compounds of the general formula I are those in which $R^3$ denotes an —$NR^4R^5$ group and in each case the remaining residues $R^1$, $R^2$, $R^8$, $R^9$ and A have the above-stated meaning, optionally in each case in the form of the pure stereoisomers thereof, in particular enantiomers or diastereomers, the racemates thereof or in the form of mixtures of the stereoisomers, in particular the enantiomers and/or diastereomers, in any desired mixing ratio, or in each case in the form of corresponding salts or in each case in the form of corresponding solvates.

Likewise preferred substituted cyclopentene compounds of the general formula I are those in which $R^4$ and $R^5$, identical or different, in each case denote hydrogen or a linear or branched $C_{1-6}$ alkyl residue, preferably in each case hydrogen or a linear or branched $C_{1-4}$ alkyl residue, particularly preferably in each case hydrogen, a methyl residue or an ethyl residue, very particularly preferably both simultaneously denote a methyl residue, and in each case the remaining residues $R^1$ to $R^3$, $R^6$–$R^9$ and A have the above-stated meaning, optionally in each case in the form of the pure stereoisomers thereof, in particular enantiomers or diastereomers, the racemates thereof or in the form of mixtures of the stereoisomers, in particular the enantiomers and/or diastereomers, in any desired mixing ratio, or in each case in the form of corresponding salts or in each case in the form of corresponding solvates.

Further preferred substituted cyclopentene compounds of the general formula I are those in which $R^6$ and $R^7$, together with the nitrogen atom bridging them as a ring member, form a saturated, optionally at least mono-substituted, 5- to 8-membered heterocyclic residue optionally comprising at least one further heteroatom as a ring member, preferably an optionally at least mono-substituted pyrrolidine, piperidine, hexamethylenimine or morpholine ring, and in each case the remaining residues $R^1$–$R^5$, $R^8$, $R^9$ and A have the above-stated meaning, optionally in each case in the form of the pure stereoisomers thereof, in particular enantiomers or diastereomers, the racemates thereof or in the form of mixtures of the stereoisomers, in particular the enantiomers and/or diastereomers, in any desired mixing ratio, or in each case in the form of corresponding salts or in each case in the form of corresponding solvates.

Preferred substituted cyclopentene compounds of the general formula I are also those in which A denotes a —C(=O) group and in each case the remaining residues $R^1$ to $R^9$ have the above-stated meaning, optionally in each case in the form of the pure stereoisomers thereof, in particular enantiomers or diastereomers, the racemates thereof or in the form of mixtures of the stereoisomers, in particular the enantiomers and/or diastereomers, in any desired mixing ratio, or in each case in the form of corresponding salts or in each case in the form of corresponding solvates.

Likewise preferred substituted cyclopentene compounds of the general formula I are those in which $R^9$ denotes a linear or branched $C_{1-6}$ alkyl residue, preferably a linear or branched $C_{1-4}$ alkyl residue, particularly preferably a methyl residue, and in each case the residues $R^1$ to $R^8$ and A have the above-stated meaning, in each case optionally in the form of the pure stereoisomers thereof, in particular enantiomers or diastereomers, the racemates thereof or in the form of mixtures of the stereoisomers, in particular the enantiomers and/or diastereomers, in any desired mixing ratio, or in each case in the form of corresponding salts or in each case in the form of corresponding solvates.

Particularly preferred substituted cyclopentene compounds of the general formula I are those selected from the group consisting of 2-(3,5-difluorophenyl)-5-dimethylaminomethyl-3-(4-methanesulfonylphenyl)-cyclopent-2-enone, 5-dimethylaminomethyl-3-(4-methanesulfonylphenyl)-2-m-tolyl-cyclopent-2-enone,
5-dimethylaminomethyl-2-(3-hydroxyphenyl)-3-(4-methanesulfonylphenyl)-cyclopent-2-enone,
5-dimethylaminomethyl-2-(4-fluorophenyl)-3-(4-methanesulfonylphenyl)-cyclopent-2-enone,
5-dimethylaminomethyl-2-(3-fluorophenyl)-3-(4-methanesulfonylphenyl)-cyclopent-2-enone,
2-(3-chlorophenyl)-5-dimethylaminomethyl-3-(4-methanesulfonylphenyl)-cyclopent-2-enone,
5-dimethylaminomethyl-3-(4-methanesulfonylphenyl)-2-p-tolyl-cyclopent-2-enone,
5-dimethylaminomethyl-2-(4-hydroxyphenyl)-3-(4-methanesulfonylphenyl)-cyclopent-2-enone,
5-dimethylaminomethyl-3-(4-methanesulfonylphenyl)-2-(3-trifluoromethylphenyl)-cyclopent-2-enone,
5-dimethylaminomethyl-3-(4-methanesulfonylphenyl)-2-(4-methoxyphenyl)-cyclopent-2-enone,
2-benzo[1,3]dioxol-5-yl-5-dimethylaminomethyl-3-(4-methanesulfonylphenyl)-cyclopent-2-enone,
2-(3,5-dichlorophenyl)-5-dimethylaminomethyl-3-(4-methanesulfonylphenyl)-cyclopent-2-enone,
5-dimethylaminomethyl-3-(4-methanesulfonylphenyl)-2-(3-methoxyphenyl)-cyclopent-2-enone,
5-dimethylaminomethyl-2-(4-fluoro-3-methylphenyl)-3-(4-methanesulfonylphenyl)-cyclopent-2-enone,
2-(4-tert-butylphenyl)-5-dimethylaminomethyl-3-(4-methanesulfonylphenyl)-cyclopent-2-enone,
5-dimethylaminomethyl-2-(3-ethoxyphenyl)-3-(4-methanesulfonylphenyl)-cyclopent-2-enone,
5-dimethylaminomethyl-2,3-bis-(4-methanesulfonylphenyl)-cyclopent-2-enone,
5-dimethylaminomethyl-3-(4-methanesulfonylphenyl)-2-naphth-2-yl-cyclopent-2-enone,
5-dimethylaminomethyl-2-(3,4-dimethylphenyl)-3-(4-methanesulfonylphenyl)-cyclopent-2-enone,
5-dimethylaminomethyl-2-(3-isopropylphenyl)-3-(4-methanesulfonylphenyl)-cyclopent-2-enone,
2-(4-tert-butylphenyl)-5-dimethylaminomethyl-3-(4-methanesulfonylphenyl)-cyclopent-2-enol,
acetic acid 2-(4-tert-butylphenyl)-5-dimethylaminomethyl-3-(4-methanesulfonylphenyl)-cyclopent-2-enyl ester,
5-dimethylaminomethyl-3-(4-methanesulfonylphenyl)-2m-tolyl-cyclopent-2-enol, and in each case corresponding salts, preferably hydrochlorides, and in each case corresponding solvates, preferably hydrates.

The present invention also provides a process for production of substituted cyclopentene compounds of the above-stated general formula I, in accordance with which at least one compound of the general formula II

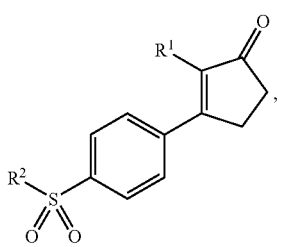

in which $R^1$ and $R^2$ have the above-stated meaning, is converted by reaction with formaldehyde and/or paraformaldehyde and at least one substituted amine compound of the general formula IIIa

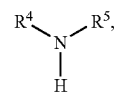

in which $R^4$ and $R^5$ have the above-stated meaning, or at least one substituted amine compound of the general formula IIIb,

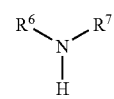

in which $R^6$ and $R^7$ have the above-stated meaning, or by reaction with at least one methylene immonium compound of the general formula IVa

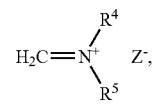

in which $R^4$ and $R^5$ have the above-stated meaning and Z denotes a chlorine, bromine or iodine atom, or with at least one methylene immonium compound of the general formula IVb,

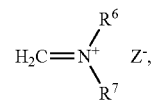

in which $R^6$ and $R^7$ have the above-stated meaning and Z denotes a chlorine, bromine or iodine atom, into a compound of the above-stated general formula I, in which $R^1$ to $R^7$ have the above-stated meaning, and A denotes a —(C=O) group, is optionally purified, optionally isolated, and is optionally converted by reaction with at least one reducing agent into a compound of the above-stated general formula I, in which $R^1$ to $R^7$ have the above-stated meaning, A denotes a C(H)($R^8$) group and $R^8$ denotes a hydroxy group, is optionally purified, optionally isolated, and this compound is optionally converted by reaction with an esterification reagent into a compound of the above-stated general formula I, in which $R^1$ to $R^7$ have the above-stated meaning, A denotes a C(H)($R^8$) group and $R^8$ an —O(C=O)—$R^9$ group, in which $R^9$ has the above-stated meaning, and this compound is optionally purified and optionally isolated.

The compounds of the general formula II may be produced in accordance with conventional methods known to the person skilled in the art, such as for example described in D. Zhao et al., Tetrahedron 1999, 55, pages 6001–6018 and W. Cameron Black et al., J. Med. Chem., 1999, 42, pages 1274–1281. The corresponding description is hereby introduced as a reference and is deemed to be part of the disclosure. Compounds IIIa, IIIb, IVa, and IVb may likewise be obtained in accordance with conventional methods known to the person skilled in the art or be purchased commercially.

The reaction of compounds of the general formula II with formaldehyde and/or paraformaldehyde and with compounds of the general formulae IIIa or IIIb may preferably be performed in a polar reaction medium such as water, alcohols, acetic acids or in a mixture of at least two of these reaction media.

The reaction of compounds of the general formula II with compounds of the general formulae IVa or IVb may preferably be performed in a reaction medium based on acetonitrile and/or tetrahydrofuran.

Temperature and pressure may vary within a wide range during these above-stated reactions. The reaction with compounds of the general formula IIIa or IIIb preferably proceeds at a temperature of 10° C. up to the boiling temperature of the reaction medium, preferably of 20° C. up to the boiling temperature of the reaction medium. The reaction with compounds of the general formula IVa and IVb preferably proceeds at a temperature of 10 to 55° C., particularly preferably at a temperature of 20 to 50° C.

The reduction of compounds of the general formula I, in which A denotes a —(C=O) group, to yield compounds of the general formula I, in which A denotes a C(H)(R$^8$) group, may proceed in accordance with conventional methods known to the person skilled in the art using conventional reducing agents and reaction media known to the person skilled in the art.

The person skilled in the art will understand that the reducing agent(s) should be selected such that the double bond of the cyclopentene ring is not attacked. The reducing agents used are preferably complex borohydrides and/or complex aluminium hydrides, particularly preferably sodium borohydride.

Preferred reaction media for the reduction are alcohols, in particular methanol, or mixtures based on alcohols, in particular methanol. The reduction is preferably performed at a temperature of 10 to 60° C., preferably of 20 to 50° C. The reduction with sodium borohydride particularly preferably proceeds in methanol at a temperature of 20 to 50° C.

The esterification of compounds of the general formula I, in which A denotes a C(H)(R$^8$) group and R$^8$ denotes an OH group and in each case the remaining residues R$^1$ to R$^7$ have the above-stated meaning, may be performed in accordance with conventional methods known to the person skilled in the art, as for example described in Barth, Organikum, DeutscherVerlag derWissenschaften, 19th edition 1993, pages 422–424. The corresponding description is hereby introduced as a reference and is deemed to be part of the disclosure.

The esterification preferably proceeds by reaction with carboxylic acid chlorides of the general formula R$^9$—(C=O)—Cl or with carboxylic anhydrides of the general formula R$^9$—(C=O)—O—(C=O)—R$^9$, in which R$^9$ in each case has the above-stated meaning.

The process according to the invention may also be performed in part or completely in semi- or fully automated form as a parallel synthesis of a plurality of cyclopentene compounds according to the invention of the above-stated general formula I.

The salts of the substituted cyclopentene compounds according to the invention of the above-stated general formula I may be obtained in accordance with conventional methods known to the person skilled in the art, for example by reaction of the particular compound of the general formula I or of a corresponding stereoisomer, in the form of the free base with one or more inorganic acids and/or one or more organic acids. The reaction preferably proceeds with an acid selected from the group consisting of perchloric acid, hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, saccharin, cyclohexanesulfamic acid, aspartame, sebacic acid monomethyl ester, 5-oxo-proline, hexane-1-sulfonic acid, nicotinic acid, 2-aminobenzoic acid, 3-aminobenzoic acid or 4-aminobenzoic acid, 2,4,6-trimethylbenzoic acid, α-lipoic acid, acetylglycine, acetylsalicylic acid, hippuric acid and aspartic acid.

The substituted cyclopentene compounds of the above-stated general formula I and optionally in each case the corresponding stereoisomers thereof and in each case the salts thereof, are obtained using conventional methods known to the person skilled in the art in the form of the solvates thereof, in particular hydrates.

If the substituted cyclopentene compounds according to the invention of the general formula I are obtained after the production thereof in the form of the stereoisomers thereof, preferably in the form of the racemates thereof or other mixtures of their various enantiomers and/or diastereomers, these may be separated and optionally isolated by conventional processes known to the person skilled in the art. Examples are chromatographic separation processes, in particular liquid chromatography processes at standard pressure or at elevated pressure, preferably MPLC and HPLC processes, and fractional crystallisation processes. Individual enantiomers, e.g. diastereomeric salts formed by means of HPLC on a chiral phase or by means of crystallisation with chiral acids, for instance (+)-tartaric acid, (−)-tartaric acid or (+)-10-camphorsulfonic acid, may here in particular be separated from one another.

It has now surprisingly been found that these substituted cyclopentene compounds according to the invention of the general formula I, optionally the corresponding stereoisomers thereof, in each case corresponding salts and in each case corresponding solvates are distinguished by an elevated affinity to the CGRP receptor, in particular to the CGRP1 receptor, and act as CGRP antagonists, in particular CGRP1 antagonists. These compounds are accordingly ideally suited to regulating the CGRP receptor, in particular the CGRP1 receptor.

The substituted cyclopentene compounds according to the invention of the above-stated general formula I and optionally corresponding stereoisomers and in each case the corresponding salts and in each case the corresponding solvates are toxicologically safe and are thus suitable as pharmaceutical active ingredients in pharmaceutical preparations.

The present invention accordingly also provides a pharmaceutical preparation containing at least one substituted cyclopentene compound of the above-stated general formula I, optionally in the form of the pure stereoisomer thereof, in particular enantiomer or diastereomer, the racemate thereof or in the form of a mixture of the stereoisomers, in particular the enantiomers and/or diastereomers, in any desired mixing ratio, and/or a corresponding physiologically acceptable salt and/or a corresponding solvate and optionally one or more physiologically acceptable auxiliary substances.

In a further embodiment, in addition to at least one substituted cyclopentene compound according to the invention and optionally one or more physiologically acceptable auxiliary substances, the pharmaceutical preparation according to the invention may also contain one or more further pharmacologically active active ingredients, which may preferably be selected from the group consisting of nonsteroidal antiinflammatory drugs (NSAID), triptans and ergot alkaloids.

Suitable nonsteroidal antiinflammatory drugs (NSAID), triptans and ergot alkaloids and processes for the production thereof are known to the person skilled in the art.

Nonsteroidal antiinflammatory drugs which may preferably be considered are one or more compounds selected from the group consisting of acetylsalicylic acid, naproxen, diclofenac, ibuprofen, ketoprofen, piroxicam, diflunisal, indomethacin, tolmetin and celecoxib.

Suitable triptans may preferably be selected from the group consisting of sumatriptan, eletriptan, rizatriptan, zolmitriptan and naratriptan.

If the pharmaceutical preparation according to the invention comprises one or more ergot alkaloids, these are preferably ergotamine and/or dihydroergotamine.

The pharmaceutical preparation according to the invention is preferably suitable for CGRP receptor regulation, in particular for CGRP1 receptor regulation, for the treatment and/or prevention of disorders and/or diseases which are mediated by the CGRP receptor, preferably by the CGRP-1 receptor, for the prevention and/or treatment of pain, preferably of acute pain, chronic pain, chronic inflammatory pain and/or visceral pain, cluster headaches, neurovascular disorders, migraine, preferably of migraine with aura, migraine without aura, common migraine, classic migraine or complicated migraine, inflammation, preferably pulmonary inflammation, asthma, arthritis, hypertonia, hypotonia, tachycardia, non-insulin-dependent diabetes mellitus, cardiovascular diseases, skin conditions and/or skin damage, preferably skin damage caused by heat and/or radiation, particularly preferably skin damage caused by sunburn, allergic rhinitis, diseases which accompany overshooting vascular dilation, preferably shock or sepsis, menopausal hot flushes or opioid tolerance, preferably morphine tolerance.

The present invention also provides the use of at least one substituted cyclopentene compound of the general formula I, optionally in the form of the pure stereoisomer thereof, in particular enantiomer or diastereomer, the racemate thereof or in the form of mixtures of the stereoisomers, in particular the enantiomers and/or diastereomers, in any desired mixing ratio and/or of a corresponding salt and/or of a corresponding solvate for the production of a pharmaceutical preparation for CGRP receptor regulation, in particular for CGRP1 receptor regulation, for the treatment and/or prevention of disorders and/or diseases which are mediated by the CGRP receptor, preferably by the CGRP-1 receptor, for the prevention and/or treatment of pain, preferably of acute pain, chronic pain, chronic inflammatory pain and/or visceral pain, cluster headaches, neurovascular disorders, migraine, preferably of migraine with aura, migraine without aura, common migraine, classic migraine or complicated migraine, inflammation, preferably pulmonary inflammation, asthma, arthritis, hypertonia, hypotonia, tachycardia, non-insulin-dependent diabetes mellitus, cardiovascular diseases, skin conditions and/or skin damage, preferably skin damage caused by heat and/or radiation, particularly preferably skin damage caused by sunburn, allergic rhinitis, diseases which accompany overshooting vascular dilation, preferably shock or sepsis, menopausal hot flushes or opioid tolerance, preferably morphine tolerance.

It is particularly preferred to use at least one substituted cyclopentene compound of the above-stated general formula I, optionally in the form of the pure stereoisomers thereof, in particular enantiomer or diastereomer, the racemate thereof or in the form of mixtures of the stereoisomers, in particular the enantiomers and/or diastereomers, in any desired mixing ratio, and/or of a corresponding salt and/or of a corresponding solvate, for the production of a pharmaceutical preparation for the prevention and/or treatment of pain, preferably acute pain, chronic pain, chronic inflammatory pain or visceral pain, cluster headaches, neurovascular disorders, of migraine, preferably of migraine with aura, migraine without aura, common migraine, classic migraine or complicated migraine, of inflammation, preferably pulmonary inflammation, or of asthma, very particularly preferably for the prevention and/or treatment of pain, preferably acute pain, chronic pain, chronic inflammatory pain or visceral pain, cluster headaches, migraine with aura, migraine without aura, common migraine, classic migraine or complicated migraine.

It is likewise preferred to use at least one substituted cyclopentene compound of the above-stated general formula I, optionally in the form of the pure stereoisomer thereof, in particular enantiomer or diastereomer, the racemate thereof or in the form of mixtures of the stereoisomers, in particular the enantiomers and/or diastereomers, in any desired mixing ratio, and/or of a corresponding salt and/or of a corresponding solvate, in combination with one or more further pharmacologically active active ingredients, preferably selected from the group consisting of nonsteroidal antiinflammatory drugs, triptans and ergot alkaloids, for the production of a pharmaceutical preparation for the prevention and/or treatment of pain, preferably acute pain, chronic pain, chronic inflammatory pain or visceral pain, cluster headaches, neurovascular disorders, of migraine, preferably of migraine with aura, migraine without aura, common migraine, classic migraine or complicated migraine, of inflammation, preferably pulmonary inflammation, or of asthma.

The substituted cyclopentene compounds according to the invention of the above-stated general formula I and optionally in each case corresponding stereoisomers may, as described above, also be obtained in the form of the physiologically acceptable salts thereof, wherein the pharmaceutical preparation according to the invention may comprise one or more salts of one or more of these compounds.

The pharmaceutical preparation according to the invention may be formulated as a liquid, semisolid or solid dosage form, for example in the form of solutions for injection, drops, succi, syrups, sprays, suspensions, tablets, patches, capsules, dressings, suppositories, ointments, creams, lotions, gels, emulsions, aerosols or in multiparticulate form, for example in the form of pellets or granules, optionally pressed into tablets, packaged in capsules or suspended in a liquid, and may also be administered as such.

In addition to one or more of the substituted cyclopentene compounds of the above-stated general formula I, optionally in the form of the pure stereoisomer thereof, in particular enantiomer or diastereomer, the racemate thereof or in the form of mixtures of the stereoisomers, in particular the enantiomers and/or diastereomers, in any desired mixing ratio, and/or a corresponding salt and/or a corresponding solvate, the pharmaceutical preparation according to the invention conventionally contains further physiologically acceptable pharmaceutical auxiliary substances, which are preferably selected from the group consisting of matrix materials, fillers, solvents, diluents, surface-active substances, dyes, preservatives, disintegrants, slip agents, lubricants, aromas and binders.

Selection of the physiologically acceptable auxiliary substances and the quantities thereof which are to be used depends upon how the pharmaceutical preparation is to be administered, for example orally, subcutaneously, parenterally, intravenously, intraperitoneally, intradermally, intramuscularly, intranasally, buccally, rectally or topically, for example onto infections of the skin, mucous membranes or eyes.

Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration.

Cyclopentene compounds according to the invention in a depot in dissolved form or in a dressing, optionally with the addition of skin penetration promoters, are suitable percutaneous administration preparations.

Orally or percutaneously administrable formulations in particular may also release the particular substituted cyclopentene compounds in delayed manner.

Production of the pharmaceutical preparations according to the invention may proceed with the assistance of conventional means, devices, methods and processes known to the person skilled in the art, such as are described for example in "Remington's Pharmaceutical Sciences", Ed. A. R. Gennaro, 17th ed., Mack Publishing Company, Easton, Pa. (1985), in particular in part 8, chapters 76 to 93. The corresponding description is hereby introduced as a reference and is deemed to be part of the disclosure.

The quantity of the substituted cyclopentene compounds according to the invention to be administered to the patient may vary and is for example dependent on the weight or age of the patient and on the mode of administration, the indication and the severity of the complaint. Conventionally, at least one substituted cyclopentene compound according to the invention is administered in a quantity of 0.005 to 500 mg/kg, preferably of 0.01 to 50 mg/kg, of patient body weight.

Pharmacological Methods:

(A) Investigation of the Inhibition of Binding of $[^{125}I]$-α-CGRP to the Human CGRP1 Receptor Various CGRP receptor subtypes are known which in each case consist of a complex of CRLR (Calcitonin Receptor-Like Receptor), RAMP (Receptor-Associated Membrane Protein) and RCP (Receptor Component Protein).

Investigation of the inhibition of the binding of 3-$[^{125}I]$-iodohistidyl[10]-α-CGRP is carried out on a human CGRP1 receptor, which is composed of the recombinant human constituents (Calcitonin Receptor-Like Receptor) CRLR and (Receptor-Associated Membrane Protein) RAMP1 (item no. ES420-M9, Euroscreen, Belgium).

The radioligand used is 3-$[^{125}I]$-iodohistidyl[10] Calcitonin Gene-Related Peptide (Amersham pharmacia biotech, code IM 184, 2000 Ci/mmol).

The binding studies are performed as SPA (scintillation proximity assay) batches with WGA beads (wheat germ agglutinin, Amersham pharmacia biotech, code: RPNQ 0001). The incubation buffer used is 50 mm tris pH 7.4 with 120 mM NaCl, 5 mM KCl and 5 mM $MgCl_2$. 0.25 µg of protein of membrane suspension of CHO-K1 cells, 250 µg of beads and 10 µg of albumin (BSA) and the above-stated radioligand in a concentration of 100 µM together with the compound according to the invention to be investigated in a concentration of 10 µM are introduced into each well of a microtitre plate.

After an incubation period of 90 minutes, radioactivity is measured in a Trilux detector (Wallac, Finland).

(B) Investigation of the Action of the Compounds According to the Invention on the Formation of cAMP in the Human Neuroblastoma Cell Line SK-N-MC.

Cells of the human neuroblastoma cell line SK-N-MC express endogenous CGRP receptors of elevated affinity, which mediate activation of adenylate cyclase, as described in Van Valen et al., "Calcitonin gene-related peptide (CGRP) receptors are linked to cyclic adenosine monophosphate production in SK-N-MC human neuroblastoma cells", Neuroscience Lett., 119, pages 195–198 (1990). The corresponding description is hereby introduced as a reference and is deemed to be part of the disclosure. 3',5'-cyclic AMP (cAMP) is measured with a competitive immunoassay as described.

Material & Methods

Cell Culture:

Human SK-N-MC cells (DSMZ, Braunschweig, Germany) are cultured in Dulbecco's minimal essential medium (DMEM high glucose 4.5 mg/l), which is combined with 10% (volume/volume) of heat-activated foetal calf serum, 2 mM of L-glutamine and 0.1 mM of non-essential amino acids (NEM, Gibco BRL, cat. no.11140-035, L-alanine 890 mg/l, L-asparagine 1320 mg/l, L-aspartic acid 1330 mg/l, L-glutamic acid 1470 mg/l, glycine 750 mg/l, L-proline 1150 mg/l, L-serine 1050 mg/l). Growth proceeds at 37° C., 95% atmospheric humidity and 5% $CO_2$. $5 \times 10^4$ cells per well are sown into a 96 well microtitre plate for the cAMP determinations and, at 80% confluence approximately 48 hours later, are incubated with the substances to be tested.

Measurement of Cyclic AMP

3',5'-cyclic AMP (cAMP) is measured with the assistance of a competitive immunoassay, as described in Chiulli, A. C. et al., "A novel high throughput chemiluminiscent assay for measurement of cellulose cyclic adenosine monophosphate levels", J. Biomol. Screening 5, 239–247, 2000. The corresponding description is hereby introduced as a reference and is deemed to be part of the present disclosure.

3',5'-cyclic AMP (cAMP) is measured using the Tropic® cAMP Screen™ chemiluminescent ELISA (Applied Biosystems). This immunoassay comprises an alkaline phosphatase (AP)-labelled cAMP conjugate, a highly specific anti-cAMP antibody, precoated microtitre plates, a cAMP standard and the Tropix CSPD® substrate with luminescence enhancer. The medium of 80% confluent cells in 96-well plates is replaced by 110 µl of growth medium with 50 µl of 4 mM isobutyl-1-methylxanthine solution (IBMX, Sigma, 1 mM final concentration), 20 µl of a medium solution comprising the compound to be investigated in 10-fold concentrated form or solvent (dimethyl sulfoxide), and 20 µl of 10-fold concentrated CGRP (Calbiochem) or solvent (acetic acid). The proportion of solvent should here not exceed 0.4% (volume/volume). After incubation for 30 minutes at 37° C., the cells are pelletised and the culture medium removed. The cell pellet is incubated in 100 µl of lysis buffer (Applied Biosystems) at 37° C. until all the cells are completely lysed (usually approx. 30 minutes, verified by inspection under a microscope). Immediately before use, the cAMP-AP conjugate is diluted 1:100 volume/volume with conjugate dilution buffer. 60 µl/well of the lysate sample or the standard and 30 µl/well of the diluted cAMP-AP conjugate are added to the cavities of an assay plate (Applied Biosystems), are mixed by repeated pipetting, after which the anti-cAMP antibody (60 μl/well) is added and the contents are again mixed until homogeneous by repeated pipetting. After 1 hour's incubation at room temperature (approx. 25° C.) with shaking in the dark, the supernatant is removed and the cells washed 6 times with the washing buffer (Applied Biosystems).

Detection is performed by incubating the cells in 100 μl/well of the CSPD®/Sapphire-II ™ RTU substrate/enhancer solution for 30 minutes and measuring the signal in a luminometer (MikroBeta Trilux 1450-021, Wallac, Finland, series no. 4500593) at 1 second/well.

The substituted cyclopentene compounds according to the invention are used in 10 μM concentrations together with 1 nM CGRP. Dose-action curves are determined with human CGRP or the antagonistic truncated peptide $CGRP_{(8-37)}$ (Calbiochem; together with 1 nM CGRP) and Graph Pad Prism 3.0 software is used for the non-linear regression analysis.

(C) GTPγS Assay:

The antagonistic action of the substituted cyclopentene compounds according to the invention was determined using this assay.

To this end, membranes from CHO-K1 cells (Euroscreen, Brussels, Belgium), which are transfected with the human calcitonin receptor-related receptor (CRLR, Genbank: U17473) and human receptor-associated modifying protein type 1 (RAMP1, Genbank AJ001014), are first of all rapidly thawed, diluted in 20 mM HEPES, 10 mM NaCl, 10 mM $MgCl_2$, 1 mM EDTA pH 7.4 and resuspended by homogenisation. For each test batch, 2 μg of membrane protein are incubated in a volume of 150 μl in 20 mM HEPES pH 7.4, 10 mM $MgCl_2$, 100 mM NaCl, 1 mM EDTA, 0.1 μM CGRP, 1 μM GDP and the substance to be tested. After 30 minutes' incubation at room temperature, 50 μl of 2 nM [35S]GTPγS (Amersham) are added and incubated for a further 30 minutes at room temperature and the assay-plate is centrifuged for 10 minutes at 3200 revolutions per minute. Bound activity was determined with a Wallac 1450 Microbeta Scintillation Counter (Wallac, Torku, Finland).

(D) Determination of CGRP Receptor Affinity on Isolated, Spontaneously Beating Guinea Pig Atrium There are two CGRP receptor subtypes, CGRP1 and CGRP2. Functionally, these two subtypes may be distinguished in that the fragment $hCGRP_{(8-37)}$ more strongly inhibits the CGRP1-mediated positive inotropic and chronotropic action in guinea pig atria than the CGRP2-mediated inhibition of the twitch response in rat vas deferens. The selective CGRP2 agonist $[Cys(ET)^{2,7}]hCGRP\alpha$, in contrast, is distinctly more active on rat vas deferens (CGRP2) than on guinea pig atrium (CGRP1), as described in the published literature by Y. Dumont et al., "A potent and selective CGRP2 agonist $[Cys(ET)^{2,7}]hCGRP_{(8-37)}$: comparison in prototypical CGRP1 and CGRP2 in vitro bioassays", Can. J. Physiol. Pharmacol. 75: 671–6,1997. The corresponding literature description is hereby introduced as a reference and is deemed to be part of the disclosure.

Investigations into the action of CGRP on guinea pig atrium are accordingly suitable for quantifying CGRP1-antagonistic action in a function in vitro system.

In order to determine the CGRP1-antagonistic action of the compounds according to the invention in a functional in vitro system, the increase in cardiac frequency brought about by human α-CGRP (h-α-CGRP) is determined on spontaneously beating guinea pig atria as a parameter for CGRP1-agonistic action. The CGRP1-antagonistic action of human α-$CGRP_{(8-37)}$(h-α-$CGRP_{(8-37)}$) on this model serves as a validation for the investigation of the compounds according to the invention.

The concentration-action curve is determined with h-α-CGRP (agonist) and the compounds to be investigated (antagonists) are in each case added 5 minutes previously to the organ bath. h-α-CGRP, dissolved in dimethyl sulfoxide (DMSO), is here added cumulatively to the organ bath in concentrations of 1, 2.15, 4.64, 10, 21.5 and 46.4 nM. The exposure time for each concentration level is 2 minutes. The compounds according to the invention to be investigated in various concentrations or dimethyl sulfoxide are added with h-α-CGRP to the organ bath 5 minutes before the beginning of the concentration-action curve.

The invention is explained below with reference to Examples. These explanations are given merely by way of example and do not restrict the general concept of the invention.

EXAMPLES

Example 1

2-(3,5-Difluorophenyl)-5-dimethylaminomethyl-3-(4-methanesulfonylphenyl)-cyclopent-2-enone, hydrochloride The compound 2-(3,5-difluorophenyl)-3-(4-methanesulfonylphenyl)-cyclopent-2-enone was first produced according to the description of D. Zhao et al., Tetrahedron 1999, 55, page 6001–6018.

A solution of 1.37 g of 2-(3,5-difluorophenyl)-3-(4-methanesulfonylphenyl)-cyclopent-2-enone in 14 ml of dried acetonitrile containing 0.03 ml of acetyl chloride was then combined with 0.37 g of N,N-dimethylmethylene immonium chloride and the resultant reaction mixture was stirred for 24 hours at a temperature of 20° C. 50 ml of diethyl ether were then added and stirring performed for a further 3 hours at 20° C. A solid was obtained in this manner, which was isolated by suction filtration, washed with diethyl ether and dried under reduced pressure. 1.71 g (corresponding to 98.4% of theoretical) of 2-(3,5-difluorophenyl)-5-dimethylaminomethyl-3-(4-methanesulfonylphenyl)-cyclopent-2-enone, hydrochloride were obtained in the form of virtually colourless crystals with a melting point of 104–106° C.

Examples 2–20

The compounds according to the invention of Examples 2–20 were produced by the method described in detail in Example 1 and using the educts of the general formula II stated Table I below, these being obtained in accordance with description of D. Zhao et al., Tetrahedron 1999, 55, page 6001–6018 or of W. Cameron Black et al., J. Med. Chem. 1999,42 1274–1281.

TABLE I

| Example | Compound of the general formula II used |
|---|---|
| 2 | 3-(4-methanesulfonylphenyl)-2-m-tolyl-cyclopent-2-enone |
| 3 | 2-(3-hydroxyphenyl)-3-(4-methanesulfonylphenyl)-cyclopent-2-enone |
| 4 | 2-(4-fluorophenyl)-3-(4-methanesulfonylphenyl)-cyclopent-2-enone |
| 5 | 2-(3-fluorophenyl)-3-(4-methanesulfonylphenyl)-cyclopent-2-enone |

TABLE I-continued

| Example | Compound of the general formula II used |
|---|---|
| 6 | 2-(3-chlorophenyl)-3-(4-methanesulfonylphenyl)-cyclopent-2-enone |
| 7 | 3-(4-methanesulfonylphenyl)-2p-tolyl-cyclopent-2-enone |
| 8 | 2-(4-hydroxyphenyl)-3-(4-methanesulfonylphenyl)-cyclopent-2-enone |
| 9 | 3-(4-methanesulfonylphenyl)-2-(3-trifluoromethylphenyl)-cyclopent-2-enone |
| 10 | 3-(4-methanesulfonylphenyl)-2-(4-methoxyphenyl)-cyclopent-2-enone |
| 11 | 2-benzo[1,3]dioxol-5-yl-3-(4-methanesulfonylphenyl)-cyclopentene-2-enone |
| 12 | 2-(3,5-dichlorophenyl)-3-(4-methanesulfonylphenyl)-cyclopent-2-enone |
| 13 | 3-(4-methanesulfonylphenyl)-2-(3-methoxyphenyl)-cyclopent-2-enone |
| 14 | 2-(4-fluoro-3-methylphenyl)-3-(4-methanesulfonylphenyl)-cyclopent-2-enone |
| 15 | 2-(4-tert-butylphenyl)-3-(4-methanesulfonylphenyl)-cyclopent-2-enone |
| 16 | 2-(3-ethoxyphenyl)-3-(4-methanesulfonylphenyl)-cyclopent-2-enone |
| 17 | 2,3-bis-(4-methanesulfonylphenyl)-cyclopent-2-enone |
| 18 | 3-(4-methanesulfonylphenyl)-2-naphth-2-yl-cyclopent-2-enone |
| 19 | 2-(3,4-dimethylphenyl)-3-(4-methanesulfonylphenyl)-cyclopent-2-enone |
| 20 | 2-(3-isopropylphenyl)-3-(4-methanesulfonylphenyl)-cyclopent-2-enone |

Example 2

5-Dimethylaminomethyl-3-(4-methanesulfonylphenyl)-2-m-tolyl-cyclopent-2-enone, hydrochloride. Melting point: 148–150° C.

Example 3

5-Dimethylaminomethyl-2-(3-hydroxyphenyl)-3-(4-methanesulfonylphenyl)-cyclopent-2-enone, hydrochloride. Melting point: 162–164° C.

Example 4

5-Dimethylaminomethyl-2-(4-fluorophenyl)-3-(4-methanesulfonylphenyl)-cyclopent-2-enone, hydrochloride. Melting point: from 112° C. with decomposition.

Example 5

5-Dimethylaminomethyl-2-(3-fluorophenyl)-3-(4-methanesulfonylphenyl)-cyclopent-2-enone, hydrochloride. Melting point: 154–158° C.

Example 6

2-(3-Chlorophenyl)-5-dimethylaminomethyl-3-(4-methanesulfonylphenyl)-cyclopent-2-enone, hydrochloride. Melting point: 156–158° C.

Example 7

5-Dimethylaminomethyl-3-(4-methanesulfonylphenyl)-2-p-tolyl-cyclopent-2-enone, hydrochloride. Melting point: 127–129° C.

Example 8

5-Dimethylaminomethyl-2-(4-hydroxyphenyl)-3-(4-methanesulfonylphenyl)-cyclopent-2-enone, hydrochloride. Melting point: 98–100° C.

Example 9

5-Dimethylaminomethyl-3-(4-methanesulfonylphenyl)-2-(3-trifluoromethylphenyl)-cyclopent-2-enone, hydrochloride. Melting point: 152–154° C.

Example 10

5-Dimethylaminomethyl-3-(4-methanesulfonylphenyl)-2-(4-methoxyphenyl)-cyclopent-2-enone, hydrochloride. Melting point from 92° C. with decomposition.

Example 11

2-Benzo[1,3]dioxol-5-yl-5-dimethylaminomethyl-3-(4-methanesulfonylphenyl)-cyclopent-2-enone, hydrochloride. Melting point: 149–152° C.

Example 12

2-(3,5-Dichlorophenyl)-5-dimethylaminomethyl-3-(4-methansulfonylphenyl)-cyclopent-2-enone, hydrochloride. Melting point: 160–163° C.

Example 13

5-Dimethylaminomethyl-3-(4-methanesulfonylphenyl)-2-(3-methoxyphenyl)-cyclopent-2-enone, hydrochloride. Melting point: 154–157° C.

Example 14

5-Dimethylaminomethyl-2-(4-fluoro-3-methylphenyl)-3-(4-methanesulfonylphenyl)-cyclopent-2-enone, hydrochloride. Melting point: 95–98° C. with decomposition.

Example 15

2-(4-tert-butylphenyl)-5-dimethylaminomethyl-3-(4-methanesulfonylphenyl)-cyclopent-2-enone, hydrochloride. Melting point: 182–184° C.

Example 16

5-Dimethylaminomethyl-2-(3-ethoxyphenyl)-3-(4-methanesulfonylphenyl)-cyclopent-2-enone, hydrochloride. Melting point: 149–151° C.

Example 17

5-Dimethylaminomethyl-2,3-bis-(4-methanesulfonylphenyl)-cyclopent-2-enone, hydrochloride. Melting point: 157–159° C.

Example 18

5-Dimethylaminomethyl-3-(4-methanesulfonylphenyl)-2-naphth-2-yl-cyclopent-2-enone, hydrochloride. Melting point: 163–165° C.

Example 19

5-Dimethylaminomethyl-2-(3,4-dimethylphenyl)-3-(4-methanesulfonylphenyl)-cyclopent-2-enone, hydrochloride. Melting point: 139–142° C.

Example 20

5-Dimethylaminomethyl-2-(3-isopropylphenyl)-3-(4-methanesulfonylphenyl)-cyclopent-2-enone hydrochloride. Melting point: 131–133° C.

Example 21

2-(4-tert-Butylphenyl)-5-dimethylaminomethyl-3-(4-methanesulfonylphenyl)-cyclopent-2-enol, hydrochloride A solution of 1.62 g of the 2-(4-tert-butylphenyl)-5-dimethylaminomethyl-3-(4-methanesulfonylphenyl)-cyclopent-2-enone, hydrochloride obtained according to Example 15 in 15 ml methanol was combined in portions with 0.40 g of sodium borohydride with stirring at a temperature of 20° C. Once addition was complete, the resultant reaction mixture was stirred for a further three hours and completely evaporated under reduced pressure. The residue was redissolved in 50 ml of distilled water and adjusted to a pH value of 11 with addition of potassium carbonate. Extraction was then performed three times with 20 ml portions of ethyl acetate and the combined extracts were washed with saturated sodium chloride solution, dried over sodium sulfate and evaporated under reduced pressure. The resultant residue was purified by column chromatography on silica gel 60 (0.040–0.063 mm; E. Merck, Darmstadt, Germany) with a mixture of methanol and ethyl acetate in the ratio of 3:1 as eluent. 0.75 g of 2-(4-tert-butylphenyl)-5-dimethylaminomethyl-3-(4-methanesulfonylphenyl)-cyclopent-2-enol were obtained in the form of a colourless oil. This oil was redissolved in 25 ml of ethyl acetate and combined dropwise with stirring with 2 ml of a solution of hydrogen chloride in diethyl ether (5 wt. % HCl). A crystalline solid was obtained, which was isolated by suction filtration, washed with diethyl ether and dried under reduced pressure. 0.73 g of 2-(4-tert-butylphenyl)-5-dimethylaminomethyl-3-(4-methanesulfonylphenyl)-cyclopent-2-enol, hydrochloride (corresponding to 44.8% of theoretical) were obtained in the form of colourless crystals with a melting point of 223 to 224° C.

Example 22

Acetic acid 2-(4-tert-Butylphenyl)-5-dimethylaminomethyl-3-(4-methanesulfonylphenyl)-cyclopent-2-enyl ester, hydrochloride 0.37 g of the 2-(4-tert-butylphenyl)-5-dimethylaminomethyl-3-(4-methanesulfonylphenyl)-cyclopent-2-enol compound obtained according to Example 21 in the form of the free base were dissolved in 9 ml of dried tetrahydrofuran and the solution was combined with 0.24 ml of pyridine. Within 30 minutes, two 0.25 ml portions of acetic anhydride were added dropwise thereto at 20° C. with stirring and the resultant mixture was stirred for one hour at 40° C. The reaction mixture was then evaporated to a volume of approx. 2 ml, combined with 20 ml of distilled water and adjusted with potassium carbonate to a pH value of 11. Extraction was then performed three times with 10 ml portions of ethyl acetate, the combined extracts were washed with a saturated sodium chloride solution, dried over sodium sulfate and evaporated under reduced pressure. The resultant residue was purified by column chromatography on silica gel 60 (0.040–0.063 mm; E. Merck, Darmstadt, Germany) with a mixture of ethyl acetate and methanol in the ratio of 4:1 as eluent. After conversion into the corresponding hydrochloride salt according to the method stated in Example 21, 0.27 g (corresponding to 61.6% of the theoretically calculated yield) of acetic acid 2-(4-tert-butylphenyl)-5-dimethylaminomethyl-3-(4-methanesulfonylphenyl)-cyclopent-2-enyl ester, hydrochloride were obtained in the form of colourless crystals, which melted from 128° C. with decomposition.

Example 23

5-Dimethylaminomethyl-3-(4-methanesulfonylphenyl)-2m-tolyl-cyclopent-2-enol, hydrochloride 2.28 g of 5-dimethylaminomethyl-3-(4-methanesulfonylphenyl)-2m-tolyl-cyclopent-2-enone were reacted in a manner similar to the method described in Example 21 with 0.62 g of sodium borohydride to yield 5-dimethylaminomethyl-3-(4-methanesulfonylphenyl)-2m-tolyl-cyclopent-2-enol. After purification by column chromatography and precipitation of the hydrochloride with a hydrogen chloride/diethyl ether mixture, 0.95 g (corresponding to 41.4% of theoretical) were obtained in the form of colourless crystals with a melting point of 165–167° C.

Pharmacological Data:

(A) Investigation of Inhibition of Binding of 3-[$^{125}$I]-iodohistidyl$^{10}$ α-CGRP to the Human CGRP1 Receptor The inhibition of binding of 3-[$^{125}$I]-iodohistidyl$^{10}$ Calcitonin Gene-Related Peptide to the recombinant human CGRP1 receptor was determined in accordance with the method described above.

The compounds according to the invention exhibited good to very good inhibition of the binding of 3-[$^{125}$I]-iodohistidyl$^{10}$ Calcitonin Gene-Related Peptide to the recombinant human CGRP1 receptor. The values for some compounds according to the invention are shown in Table (A) below.

TABLE A

| Compound according to Example | Inhibition in % [at a concentration of 10 μM of the particular compound] |
|---|---|
| 13 | 60 |
| 3 | 66 |
| 5 | 58 |
| 1 | 40 |
| 21 | 26 |

(B) Investigation of the Action of the Compounds according to the Invention on the Formation of cAMP in the Human Neuroblastoma Cell Line SK-N-MC:

In accordance with the above-described method, CGRP potency (EC$_{50}$) was determined at 0.12 nM and the IC$_{50}$ value of CGRP8-37 (together with 1 nM CGRP) was determined at 1.57 nM to validate the method.

In three independent tests, each of which consisted of a triplicate measurement, the substituted cyclopentene compounds according to the invention exhibited very good inhibition of the CGRP-induced increase in cAMP concentration.

The values for some compounds according to the invention are shown in Table (B) below.

TABLE B

| Compound according to Example: | Inhibition of cAMP formation (at 1 nM CGRP) [in %]: |
|---|---|
| 13 | 88 |
| 3 | 86 |
| 5 | 82 |
| 1 | 71 |

(C) GTPγS Assay

The inhibition of CGRP-induced incorporation of [$^{35}$S] GTPγS into membranes was determined in accordance with the above-described method.

The compounds according to the invention are capable of inhibiting CGRP-induced incorporation of [$^{35}$S]GPγS into the membranes and thus act as CGRP receptor antagonists.

The values for some compounds according to the invention are shown in Table (C) below:

TABLE (C)

| Compound according to Example [Concentration in each case 12.5 μM] | % inhibition of CGRP-induced [35S]GTP$_\gamma$-S incorporation [concentration - CGRP of 0.1 μM] |
|---|---|
| 1 | 65.1 |
| 3 | 65.1 |
| 13 | 63.9 |
| 5 | 62.4 |

(D) Determination of CGRP Receptor-Affinity on Isolated, Spontaneously Beating Guinea Pig Atrium:

The validation and investigation of the substituted cyclopentene compounds according to the invention for their antagonistic action proceeded in accordance with the above-described method.

In the validation experiment, h-α-CGRP$_{(8-37)}$ in concentrations of 30, 100 and 300 nM gave rise to a concentration-dependent reduction in the increase in the frequency of beating of the atria, which were stimulated by h-α-CGRP. The concentration of h-α-CGRP$_{(8-37)}$ which brought about semimaximal action (IC$_{50}$) was 0.019 μM.

In the presence of vehicle solution, h-α-CGRP increased the frequency of beating of the isolated atria by approx. 35%. This positive chronotropic action, which is mediated by means of the CGRP1 receptors, was reduced in concentration-dependent manner by the substituted cyclopentene compounds according to the invention with CGRP-agonistic action.

The IC$_{50}$ values for the CGRP-antagonistic action of some compounds according to the invention are shown in Table (D) below:

TABLE D

| Compound according to Example: | IC$_{50}$ value [in μM] |
|---|---|
| 13 | 32 |
| 3 | 77 |
| 5 | 25 |
| 1 | 13 |

The invention claimed is:

1. Substituted cyclopentene compounds of the formula I,

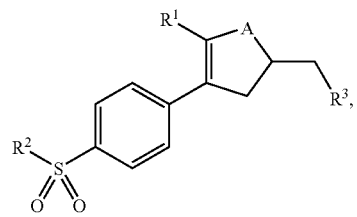

in which
R$^1$ denotes an optionally at least mono-substituted phenyl group, which may be condensed with an optionally at least mono-substituted, saturated, unsaturated or aromatic monocyclic ring system optionally comprising at least one heteroatom as a ring member,
R$^2$ denotes a linear or branched alkyl group or an —NH$_2$ group,
R$^3$ denotes an —NR$^4$R$^5$ group or an —NR$^6$R$^7$ group,
R$^4$ and R$^5$, identical or different, in each case denote hydrogen or a linear or branched alkyl group, with the proviso that the two groups R$^4$ and R$^5$ do not simultaneously mean hydrogen,
R$^6$ and R$^7$, together with the nitrogen atom bridging them as a ring member, form a saturated, optionally at least mono-substituted, heterocyclic optionally comprising at least one further heteroatom as a ring member,
A denotes a C(=O) group or a C(H) (R$^8$) group,
R$^8$ denotes an OH group or an —O—(C=O)—R$^9$ group,
R$^9$ denotes a linear or branched alkyl group,
in each case optionally in the form of the pure stereoisomers thereof, enantiomers or diastereomers, the racemates thereof or in the form of mixtures of the stereoisomers, the enantiomers and/or diastereomers, in any desired mixing ratio, or in each case in the form of corresponding salts or in each case in the form of corresponding solvates.

2. Compounds according to claim 1, characterised in that R$^1$ denotes an optionally at least mono-substituted phenyl group, which may be condensed with an optionally at least mono-substituted, saturated, unsaturated or aromatic 5- or 6-membered monocyclic ring system optionally comprising at least one heteroatom as a ring member.

3. Compounds according to claim 1, characterised in that R$^2$ denotes a linear or branched C$_{1-6}$ alkyl group or an —NH$_2$ group.

4. Compounds according to claim 1, characterised in that R$^4$ and R$^5$, identical or different, in each case denote hydrogen or a linear or branched C$_{1-6}$ alkyl group.

5. Compounds according to claim 1, characterised in that R$^6$ and R$^7$, together with the nitrogen atom bridging them as a ring member, form a saturated, optionally at least mono-substituted, 5- to 8-membered heterocyclic group optionally comprising at least one further heteroatom as a ring member.

6. Compounds according to claim 1, characterised in that A denotes a —C=(O) group.

7. Compounds according to claim 1, characterised in that R$^9$ denotes a linear or branched C$_{1-6}$ alkyl group.

8. Compounds according to claim 1 selected from the group consisting of
2-(3,5-difluorophenyl)-5-dimethylaminomethyl-3-(4-methanesulfonylphenyl)-cyclopent-2-enone, 5-dimethylaminomethyl-3-(4-methanesulfonylphenyl)-2-m-tolyl-cyclopent-2-enone,
5-dimethylaminomethyl-2-(3-hydroxyphenyl)-3-(4-methanesulfonylphenyl)-cyclopent-2-enone,
5-dimethylaminomethyl-2-(4-fluorophenyl)-3-(4-methanesulfonylphenyl)-cyclopent-2-enone,
5-dimethylaminomethyl-2-(3-fluorophenyl)-3-(4-methanesulfonylphenyl)-cyclopent-2-enone,
2-(3-chlorophenyl)-5-dimethylaminomethyl-3-(4-methanesulfonylphenyl)-cyclopent-2-enone,
5-dimethylaminomethyl-3-(4-methanesulfonylphenyl)-2-p-tolyl-cyclopent-2-enone,
5-dimethylaminomethyl-2-(4-hydroxyphenyl)-3-(4-methanesulfonylphenyl)-cyclopent-2-enone,
5-dimethylaminomethyl-3-(4-methanesulfonylphenyl)-2-(3-trifluoromethylphenyl)-cyclopent-2-enone,
5-dimethylaminomethyl-3-(4-methanesulfonylphenyl)-2-(4-methoxyphenyl)-cyclopent-2-enone,
2-benzo[1,3]dioxol-5-yl-5-dimethylaminomethyl-3-(4-methanesulfonylphenyl)-cyclopent-2-enone,
2-(3,5-dichlorophenyl)-5-dimethylaminomethyl-3-(4-methanesulfonylphenyl)-cyclopent-2-enone,
5-dimethylaminomethyl-3-(4-methanesulfonylphenyl)-2-(3-methoxyphenyl)-cyclopent-2-enone,
5-dimethylaminomethyl-2-(4-fluoro-3-methylphenyl)-3-(4-methanesulfonylphenyl)-cyclopent-2-enone,
2-(4-tert-butylphenyl)-5-dimethylaminomethyl-3-(4-methanesulfonylphenyl)-cyclopent-2-enone,
5-dimethylaminomethyl-2-(3-ethoxyphenyl)-3-(4-methanesulfonylphenyl)-cyclopent-2-enone,
5-dimethylaminomethyl-2,3-bis-(4-methanesulfonylphenyl)-cyclopent-2-enone,
5-dimethylaminomethyl-3-(4-methanesulfonylphenyl)-2-naphth-2-yl-cyclopent-2-enone,
5-dimethylaminomethyl-2-(3,4-dimethylphenyl)-3-(4-methanesulfonylphenyl)-cyclopent-2-enone,
5-dimethylaminomethyl-2-(3-isopropylphenyl)-3-(4-methanesulfonylphenyl)-cyclopent-2-enone,
2-(4-tert-butylphenyl)-5-dimethylaminomethyl-3-(4-methanesulfonylphenyl)-cyclopent-2-enol,
acetic acid 2-(4-tert-butylphenyl)-5-dimethylaminomethyl-3-(4-methanesulfonylphenyl)-cyclopent-2-enyl ester,
5-dimethylaminomethyl-3-(4-methanesulfonylphenyl)-2m-tolyl-cyclopent-2-enol,
and in each case corresponding salts, and in each case corresponding solvates.

9. A process for the production of substituted cyclopentene compounds according to claim 1, characterised in that at least one compound of the formula II

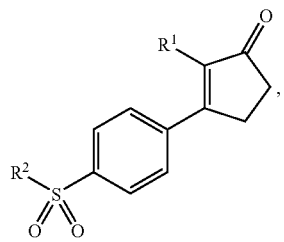

II in which $R^1$ and $R^2$ have the meaning according to claim 1, is converted by reaction with formaldehyde and/or paraformaldehyde and at least one substituted amine compound of the formula IIIa

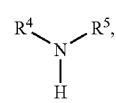

IIIa in which $R^4$ and $R^5$ have the meaning according to claim 1, or at least one substituted amine compound of the formula IIIb,

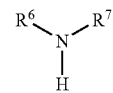

IIIb in which $R^6$ and $R^7$ have the meaning according to claim 1, or by reaction with at least one methylene immonium compound of the formula IVa

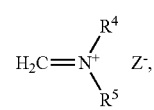

IVa in which $R^4$ and $R^5$ have the meaning according to claim 1 and Z denotes a chlorine, bromine or iodine atom, or with at least one methylene immonium compound of the formula IVb,

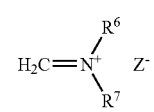

IVb in which $R^6$ and $R^7$ have the meaning according to claim 1 and Z denotes a chlorine, bromine or iodine atom, into a compound of the above-stated formula I according to claim 1, in which $R^1$ to $R^3$ have the meaning according to claim 1, and A denotes a —(C=O) group, is optionally purified, optionally isolated, and is optionally converted by reaction with at least one reducing agent into a compound of the formula I according to claim 1, in which $R^1$ to $R^3$ have the meaning according to claim 1, and A denotes a C(H) ($R^8$) group and $R^8$ denotes a hydroxy group, is optionally purified, optionally isolated, and this compound is optionally converted by reaction with an esterification reagent into a compound of the formula I, in which $R^1$ to $R^3$ have the meaning according to claim 1, A denotes a C(H) ($R^8$) group and $R^8$ an —O(C=O)—$R^9$ group, in which $R^9$ has the meaning according to claim 1, and this compound is optionally purified and optionally isolated.

10. A pharmaceutical preparation containing at least one cyclopentene compound according to claim 1 and optionally at least one further pharmacologically active active ingredient and optionally one or more physiologically acceptable auxiliary substances.

11. A pharmaceutical preparation according to claim 10, characterised in that the further pharmacologically active active ingredient is selected from the group consisting of nonsteroidal antiinflammatory drugs (NSAID), triptans and ergot alkaloids.

12. A pharmaceutical preparation according to claim 11, characterised in that the nonsteroidal antiinflammatory active ingredient is selected from the group consisting of acetylsalicylic acid, naproxen, diclofenac, ibuprofen, ketoprofen, piroxicam, diflunisal, indomethacin, tolmetin and celecoxib.

13. A pharmaceutical preparation according to claim 11, characterised in that the triptan is selected from the group consisting of sumatriptan, eletriptan, rizatriptan, zolmitriptan and naratriptan.

14. A pharmaceutical preparation according to claim 11, characterised in that ergotamine or dihydroergotamine is present as the ergot alkaloid.

15. A pharmaceutical preparation according to claim 10 for CGRP receptor regulation, for CGRP1 receptor regulation, for the treatment of disorders and/or diseases which are mediated by the CGRP receptor, the CGRP-1 receptor, for the treatment of pain, acute pain, chronic pain, chronic inflammatory pain and/or visceral pain, cluster headaches, neurovascular disorders, migraine, migraine with aura, migraine without aura, common migraine, classic migraine or complicated migraine, inflammation, pulmonary inflammation, asthma, arthritis, hypertonia, hypotonia, tachycardia, non-insulin-dependent diabetes mellitus, cardiovascular diseases, skin conditions and/or skin damage, skin damage caused by heat and/or radiation, skin damage caused by sunburn, allergic rhinitis, diseases which accompany overshooting vascular dilation, shock or sepsis, menopausal hot flushes, opioid tolerance, or morphine tolerance.

16. A method for CGRP receptor regulation, comprising administering to a patient in need thereof an effective CGRP receptor regulating amount of at least one compound according to claim 1.

17. A method for the treatment of disorders and/or diseases which are mediated by the CGRP receptor, comprising administering to a patient in need thereof a effective CGRP receptor mediating amount of at least one compound according to claim 1.

18. A mathod for the treatment of pain, comprising administering to a patient in need thereof a effective pain treating amount of at least one compound according to claim 1.

19. A method for the treatment of cluster headaches comprising administering to a patient in need thereof a effective cluster headaches treating amount of at least one compound according to claim 1.

20. A method for the treatment of neurovascular disorders comprising administering to a patient in need thereof a effective neurovascular disorder treating amount of at least one compound according to claim 1.

21. A method for the treatment of migraine, comprising administering to a patient in need thereof a effective migraine treating amount of at least one compound according to claim 1.

22. A method for the treatment of inflammation, comprising administering to a patient in need thereof a effective inflammation treating amount of at least one compound according to claim 1.

23. A method for the treatment of asthma comprising administering to a patient in need thereof a effective asthma treating amount of at least one compound according to claim 1.

24. A method for the treatment of arthritis comprising administering to a patient in need thereof a effective arthritis treating amount of at least one compound according to claim 1.

25. A method Use of at least one compound according to claim 1 for the production of a pharmaceutical preparation for the treatment of hypertonia comprising administering to a patient in need thereof a effective hypertonia treating amount of at least one compound according to claim 1.

26. A method for the treatment of hypotonia comprising administering to a patient in need thereof a effective hypotonia treating amount of at least one compound according to claim 1.

27. A method for the treatment of tachycardia comprising administering to a patient in need thereof a effective tachycardia treating amount of at least one compound according to claim 1.

28. A method for the treatment of non-insulin-dependent diabetes mellitus comprising administering to a patient in need thereof a effective non-insulin-dependent diabetes mellitus treating amount of at least one compound according to claim 1.

29. A method for the treatment of cardiovascular diseases comprising administering to a patient in need thereof a effective cardiovascular disease treating amount of at least one compound according to claim 1.

30. A method for the treatment of skin conditions and/or skin damage, comprising administering to a patient in need thereof a effective skin condition or skin damage treating amount of at least one compound according to claim 1.

31. A method for the treatment of allergic rhinitis comprising administering to a patient in need thereof a effective allergic rhinitis treating amount of at least one compound according to claim 1.

32. A method for the treatment of diseases accompanying overshooting vascular dilation, comprising administering to a patient in need thereof a effective vascular dilation modulating amount of at least one compound according to claim 1.

33. A method for the treatment of menopausal hot flushes comprising administering to a patient in need thereof a effective menopausal hot flush treating amount of at least one compound according to claim 1.

34. A method for reducing opioid tolerance, comprising administering to a patient in need thereof a effective opioid tolerance reducing amount of at least one compound according to claim 1.

35. Compounds according to claim 2, characterised in that $R^1$ denotes an optionally at least mono-substituted phenyl, naphthyl or benzo-[1,3]-dioxole group.

36. Compounds according to claim 3, characterised in that $R^2$ denotes a linear or branched $C_{1-4}$ alkyl group or an $NH_2$ group.

37. Compounds according to claim 3, characterised in that $R^2$ denotes a methyl group, en ethyl group or an $NH_2$ group.

38. Compounds according to claim 3, characterised in that $R^2$ denotes a methyl group.

39. Compounds according to claim 4, characterised in that $R^4$ and $R^5$, identical or different, in each case denote hydrogen or a linear or branched $C_{1-4}$ alkyl group.

40. Compounds according to claim 4, characterised in that $R^4$ and $R^5$, identical or different, in each case denote hydrogen, a methyl group, or an ethyl group.

41. Compounds according to claim 4, characterised in that $R^4$ and $R^5$ simultaneously denote a methyl group.

42. Compounds according to claim 5, characterised in that $R^6$ and $R^7$, together with the nitrogen atom bridging them as a ring member, form an at least mono-substituted pyrrolidine, piperidine, hexamethylenimine or morpholine ring.

43. Compounds according to claim 7, characteriseci in that $R^9$ denotes a linear or branched $C_{1-4}$ alkyl group.

44. Compounds according to claim 7, characterised in that $R^9$ denotes a methyl group.

45. Compounds according to claim 8 where the corresponding salt is the hydrochloride, and/or the corresponding solvate is the hydrate.

46. The method of claim 16 for CGRP-1 receptor regulation or for the treatment of disorders and/or diseases which are mediated by the CGRP-I receptor.

47. The method of claim 18 for the production of a pharmaceutical preparation for the treatment of acute pain, chronic pain, chronic inflammatory pain or visceral pain.

48. The method of claim 21 for the production of a pharmaceutical preparation for the treatment of migraine with aura, migraine without aura, common migraine, classic migraine or complicated migraine.

49. The method of claim 22 for the production of a pharmaceutical preparation for the treatment of pulmonary inflammation.

50. The method of claim 32 for the production of a pharmaceutical preparation for the treatment of shock or sepsis.

51. The method of claim 34 for the production of a pharmaceutical preparation for reducing morphine tolerance.

* * * * *